United States Patent [19]

Yamada et al.

[11] Patent Number: 4,692,414
[45] Date of Patent: Sep. 8, 1987

[54] APPARATUS FOR AUTOMATICALLY CONTROLLING THE FEED RATE OF ALCOHOL SOLUTION AS RAW MATERIAL IN A VINEGAR PRODUCTION PROCESS

[75] Inventors: Mikio Yamada; Yoshinori Tsukamoto; Masahiro Mizuno, all of Handa, Japan

[73] Assignee: Nakano Vinegar Co., Ltd., Aichi, Japan

[21] Appl. No.: 938,166

[22] Filed: Dec. 4, 1986

Related U.S. Application Data

[62] Division of Ser. No. 722,783, Apr. 12, 1985, Pat. No. 4,654,215.

[30] Foreign Application Priority Data

Apr. 23, 1984 [JP] Japan ................................. 59-80306

[51] Int. Cl.⁴ .............................................. C12M 1/34
[52] U.S. Cl. .................................... 435/291; 435/140; 435/818; 435/316; 426/17
[58] Field of Search ............... 435/291, 316, 140, 818, 435/287, 289, 807; 426/17

[56] References Cited

U.S. PATENT DOCUMENTS

| | | | |
|---|---|---|---|
| 1,272,276 | 7/1918 | Klein | 426/17 |
| 1,880,381 | 10/1932 | Frings | 426/17 |
| 3,445,245 | 5/1969 | Ebner | 426/17 |
| 4,378,375 | 3/1983 | Kunimatsu et al. | 426/17 |
| 4,503,078 | 3/1985 | Ebner | 426/17 |
| 4,656,140 | 4/1987 | Yamada et al. | 435/140 |

FOREIGN PATENT DOCUMENTS

| | | | |
|---|---|---|---|
| 3514634 | 11/1985 | Fed. Rep. of Germany | 426/17 |
| 57-181685 | 11/1982 | Japan | |
| 0116673 | 7/1983 | Japan | 426/17 |

Primary Examiner—James C. Yeung
Attorney, Agent, or Firm—Frishauf, Holtz, Goodman & Woodward

[57] ABSTRACT

A method and apparatus for producing vinegar by acetic acid fermentation utilizing an automatic alcohol analyzer for measurement of alcohol concentration in a fermenting broth, a feeding apparatus for feeding alcohol solution as raw material to the fermenting broth, and a control computer controllably coupled to the alcohol analyzer and to the feeding apparatus. The alcohol concentration in the fermenting broth is periodically measured by the automatic alcohol analyzer by a direction from the control computer at given intervals over a plurality of cycles of measurement; the control computer calculates a feed rate of alcohol solution as raw material to the fermenting broth so as to control the alcohol concentration in the fermenting broth at a desirable concentration on the basis of a difference between a measured alcohol concentration in the fermenting broth and a desirable alcohol concentration and the alcohol consumption rate calculated during each of the cycles by the control computer; and then the feeding apparatus is operated to control the feed rate of the alcohol solution responsive to a control signal generated by the control computer as a result of the aforementioned calculations, to thereby controllably feed alcohol solution as raw material to the fermenting broth.

9 Claims, 4 Drawing Figures

APPARATUS FOR AUTOMATICALLY CONTROLLING THE FEED RATE OF ALCOHOL SOLUTION AS RAW MATERIAL IN A VINEGAR PRODUCTION PROCESS

This is a division of application Ser. No. 722,783 filed Apr. 12, 1985, now U.S. Pat. No. 4,654,215, issued Mar. 31, 1987.

FIELD OF INVENTION

This invention relates to apparatus for automatically controlling the feed rate of an alcohol solution in a process for vinegar production by acetic acid fermetation and to apparatus for carrying out the method. More particularly, this invention relates to a method and apparatus for automatically controlling the feed rate of an alcohol solution as raw material by (i) intermittently monitoring the alcohol concentration in a fermenting broth by means of an alcohol analyzer; (ii) using a computer for control; and (iii) feeding alcohol solution as raw material to control the alcohol concentration in the fermenting broth.

BACKGROUND OF THE INVENTION

In acetic acid fermentation, since alcohol is an inhibitory substance as well as a substrate for acetic acid production, its concentration in a fermenting broth remarkably influences the fermentation productivity. If the alcohol concentration is far away from an optimal concentration, the fermentation rate not only at the present time but also at a subsequent time period of fermentation, would drop and result in a considerable decrease of the productivity of acetic acid.

However, a method for controlling the feed rate of alcohol solution as raw material on the basis of an experienced prediction of a future stage of fermentation by taking a part of a fermenting broth and measuring subsequently the alcohol concentration by means of conventional methods, such as a gas chromatography and colorimetric method, has been customarily used to carry out a monitoring. In this conventional method, it takes too much time for a series of procedures consisting of a collection of a fermenting broth for alcohol measurement and an adjustment of the feed rate after the alcohol measurement, and also the frequency of measurement is restrictive. Therefore, it is impossible to accurately follow or track the fermentation stage without excessive delays. Since the fermentation proceeds moment-by-moment, day-and-night, this conventional method is generally no longer used to always maintain the alcohol concentration in a fermenting broth optimal during fermentation.

Recently, a method which monitors the fermentation by interfacing various sensors and using a computer has become well-known. For example, in Baker's yeast fermentation, the feed rate is controlled by computer using a calculation based on the analytical result of carbon dioxide and oxygen concentration in exhaust gas. In acetic acid fermentation, it has been well-known that an important parameter is alcohol concentration in a fermenting broth as described above. However, since no equipment capable of measuring accurately and rapidly the alcohol concentration in an acetic acid fermenting broth has been developed so far, and also since a method of controlling accurately the alcohol concentration in a fermenting broth by controlling the feed rate of alcohol solution as raw material without any effect by more or less time delay has been unknown, there is no example so far of any system wherein the feed rate of alcohol solution as raw material was controlled using a computer in acetic acid fermentation.

A well-known control method which controls the feed rate on the basis of oxygen uptake with a sealed-fermentor is disclosed in Japanese Tokkyo Kokai Koho No. 57-181685. A known method which controls the feed rate of an alcohol solution on the basis of measurement of alcohol concentration using the temperature difference of boiling points gained by heating a fermenting broth taken out from a fermentor is disclosed in Japanese Tokkyo Koho No. 47-22799. However, these known methods were not satisfactory for the demand of vinegar industries which has wanted to control alcohol concentration in a fermenting broth accurately and always optimal, because these known methods have disadvantages such as that they were not useful in an opened fermentor which is, in general, used in the vinegar industry, and that they have a time delay of more than 30 minutes and, therefore, have poor accuracy of measurement in high alcohol concentrations.

SUMMARY OF THE INVENTION

According to the present invention, there is provided an apparatus for automatically controlling the feed rate of an alcohol solution in a process for producing vinegar by acetic acid fermentation utilizing an automatic alcohol analyzer for measurement of alcohol concentration in a fermenting broth, a feeding apparatus for feeding alcohol solution as raw material to the fermenting broth, and a control computer controllably coupled to the alcohol analyzer and to the feeding apparatus. The alcohol concentration in the fermenting broth is periodically measured by the automatic alcohol analyzer by a direction from the control computer at given intervals over a plurality of cycles of measurement; the control computer calculates a feed rate of alcohol solution as raw material to the fermenting broth so as to control the alcohol concentration in the fermenting broth at a desirable concentration on the basis of a difference between a measured alcohol concentration in the fermenting broth and a desirable alcohol concentration and the alcohol consumption rate calculated during each of the cycles by the control computer; and then the feeding apparatus is operated to control the feed rate of the alcohol solution responsive to a control signal generated by the control computer as a result of the aforementioned calculations, to thereby controllably feed alcohol solution as raw material to the fermenting broth.

According to another aspect of the invention, the control computer calculates a feed rate of alcohol solution as raw material to the fermenting broth so as to control the alcohol concentration in the fermenting broth at a predetermined desirable concentration according to acetic acid concentration on the basis of increasing rate of acetic acid concentration, acetic acid concentration and total concentration in the fermenting broth which are calculated by the control computer every cycle over a number of cycles at given intervals, the acetic acid concentration and total concentration being determined at a set point in an appropriate period during fermentation.

BRIEF DESCRIPTION OF THE DRAWINGS

In FIG. 2, branch (A) shows the method for controlling the alcohol concentration so as to be constant, and branch (B) shows the method for changing the alcohol concentration according to the change of acetic acid concentration;

DETAILED DESCRIPTION OF THE INVENTION

Figure 1:
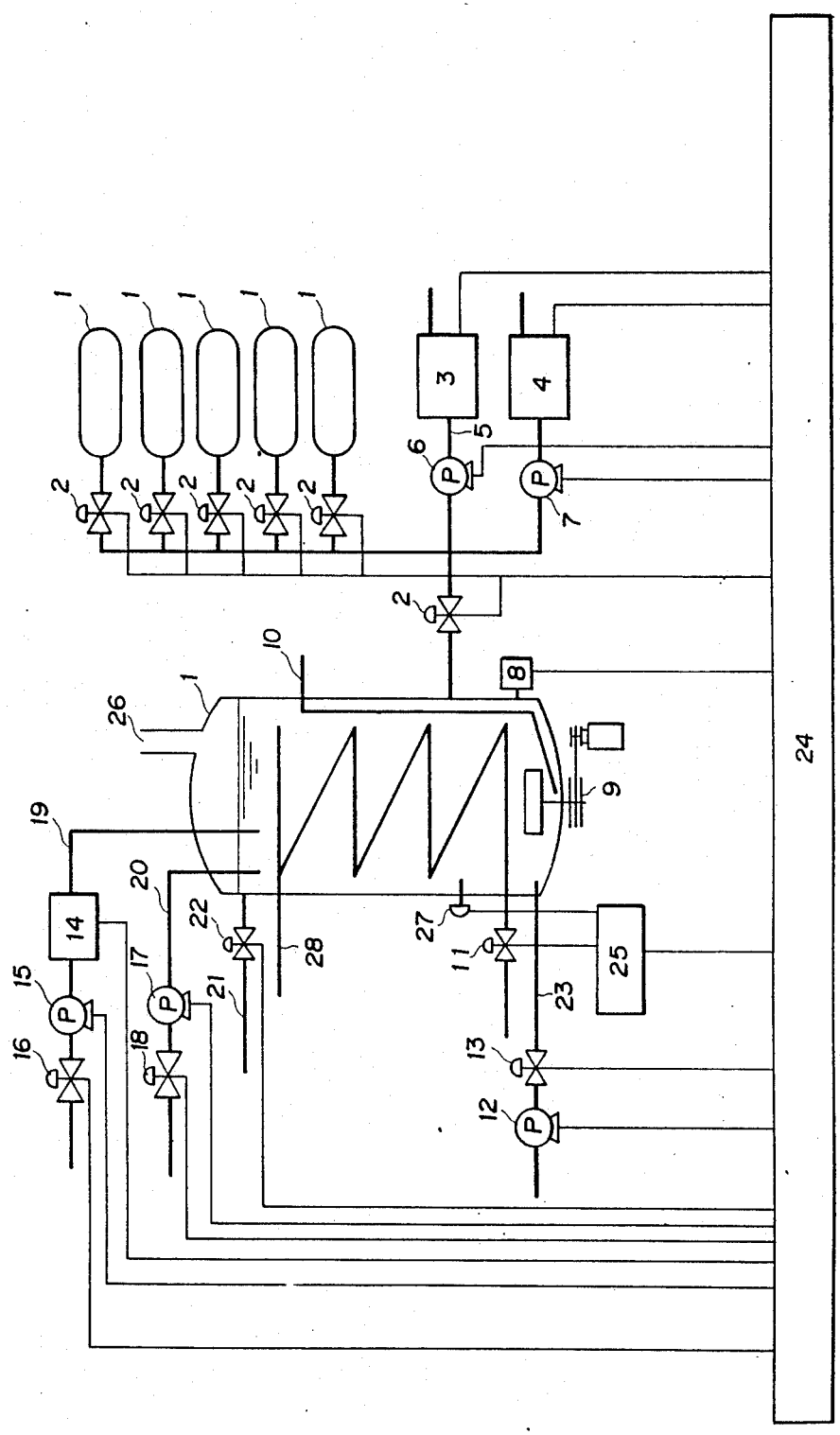
FIG. 1 is a schematic view showing an embodiment of the apparatus of this invention.

Various investigations were made on methods for controlling the feed rate of an alcohol solution as a raw material which cannot only accurately maintain the alcohol concentration in a fermenting broth constant, but which also change the alcohol concentration in correspondence to the acetic acid concentration, if necessary, for the purpose of overcoming the problems mentioned above in the conventional methods.

It was discovered that an alcohol consumption rate and an increasing rate of acetic acid concentration within a short time period from a given present time is the same as the respective rates between the given present time and a previous time it is assumed that they are not changed dramatically within a short time period such as 30 minutes to one hour. If external factors such as any operation of charge or discharge, or any change in aeration rate or agitation rate, has taken place, the alcohol consumption rate and an increasing rate of acetic acid concentration in the acetic acid fermentattion would be changed according to a fermentation stage.

As a result of the above investigations, the present inventors discovered a method for controlling the feed rate using the specific characteristic of alcohol consumption rate and an increasing rate of acetic acid concentration as mentioned above. That is, first alcohol measurements are performed twice at a short time interval, and the alcohol consumption rate and the increasing rate of acetic acid concentration are calculated using a difference of alcohol concentration or acetic acid concentration between a present time and the previous time, the feed rate of alcohol solution as raw material until the present measurement (at the "present" time), the fermentation volume and so forth. On the basis of these calculations mentioned above, the feed rate of alcohol solution as raw material is calculated to maintain the alcohol concentration aimed on the assumption that fermentation would proceed with the rates calculated above during the present measurement point and the next measurement point after a short time period.

However, the time interval for measurement in this method is limited to be 2 hours as the maximum. If the time interval is longer than 2 hours, it becomes impossible to control sufficiently the change of fermentation stage varying moment by moment and results in inaccurate control of alcohol concentration in a fermenting broth. Namely, it is essential that a series of operations such as alcohol measurement, calculation of feed rate based on the data of alcohol measurement and the control of feed rate must be performed at a frequency at least 12 times per 24 hour period, and further these operations must be carried out. Using the method of the present invention, the special skill such as prediction of the further fermentation stage becomes unnecessary.

Based on the above, the present inventors have completed a method and apparatus capable of controlling the feed rate of alcohol solution as raw material by means of repeating automatically a series of operations mentioned above, which has been difficult to accomplish by hand, at a constant time interval by connecting electrically an automatic alcohol anaylzer, an apparatus for control, and have accomplished an accurate control method which has been impossible to carry out by hand. Namely, the present invention provides a method for vinegar production which comprises, providing an automatic alcohol analyzer for measurement of alcohol concentration in a fermenting broth, an apparatus for feeding alcohol solution as raw material and a computer for control, measuring intermittently alcohol concentration by the automatic alcohol analyzer under control of the control computer, calculating the feed rate of the alcohol concentration in a fermenting broth to a desirable concentration on the basis of a difference between the alchohol concentrating in a fermenting broth and a desirable concentration and alcohol consumption rate calculated every cycle over a number of cycles by the control computer during repeating cycles, such that each output from the automatic alcohol analyzer is input into the computer, and then finally controlling the feed rate by transmitting the data calculated above to the apparatus for feeding of the alcohol solution as raw material to the feeding of the alcohol. The present invention also provides a method for vinegar production which comprises, measuring intermittently alcohol concentration by an automatic alcohol analyzer under control of a control computer as described above, calculating the feed rate of the alcohol solution as the raw material in order to control the alcohol concentration in a fermenting broth to be a predetermined concentration according to acetic acid concentration on the basis of increasing rate of acetic acid concentration, acetic acid concentration and total concentration in a fermenting broth which are calculated every cycle over a number of cycles by the control computer at repeating cycles, such that the outputs from the automatic alcohol analyzer are input into the control computer to control the acetic acid concentration and total concentration at the point set in an appropriate period in a fermentation, and controlling the alcohol feed-rate by transmitting the data resulting from the calculation into the apparatus for feeding the alcohol solution as the raw material.

The present invention also provides an apparatus for vinegar production which comprises (i) an automatic alcohol analyzer for measuring the alcohol concentration in a fermenting broth under control of a control computer and for transmitting the output corresponding to the measured alcohol concentration into the control computer; (ii) an apparatus for feeding alcohol solution as raw material to the fermenting broth and which functions to control the alcohol feed rate responsive to a signal from the control computer; and (iii) a control computer for controlling the operation of the automatic alcohol analyzer and for automatically receiving the necessary output data from the automatic alcohol analyzer and set values mentioned above to record, calculate and compare, and then supply control signals to the alcohol analyzer or apparatus to automatically control same.

According to this invention, when the time reaches the point of a given time interval, a signal for a start of the measurement is output into the automatic alcohol analyzer from the control computer. Responsive to this signal, a sampling of a fermenting broth is started and then analysis of the alcohol concentration is automatically carried out. A measured output is then transmitted from the alcohol analyzer to the control computer, and simultaneously such data as, for example, a fermentation volume, an integrated volume of fed alcohol solution of raw material, etc., are also transmitted as occasion demands, and consequently alcohol consumption rate and acetic acid production rate are instantly calculated by the control computer. On the basis of this, an alcohol feed-rate is calculated and the result is transmitted to the apparatus for feeding alcohol solution in order to control the alcohol solution feed-rate.

According to this invention, not only all the series of operations from a measurement of alcohol concentration to a control of the feed-rate of alcohol solution of raw material may be carried out without any operation by hand, but also it is possible to increase the accuracy of the control by repeating a series of operations at a short time interval, such as once every 15 minutes. Moreover, it becomes easy to control other fermentation systems by the same method in the interval of a measurement by the same method.

As described above, according to this invention, the control of the feed-rate of alcohol solution of raw material, which has heretofore required a skillful manual fermentation monitoring, may be performed automatically without manual intervention.

Now the calculation of the feed-rate of the alcohol solution of raw material is described in detail. For example, in the case of a continuous acetic acid fermentation with a submerged culture, it is characterized in that alcohol concentration (A) in a fermenting broth is remarkably lower than that in alcohol solution of raw material which is added. In the case of semi-continuous acetic acid fermentation, it is characterized in that alcohol concentration (As) of alcohol solution of raw material is high. For these circumstances, alcohol consumption rate (R) is expressed by equation (1) in both types of fermentation. Herein F and V indicate the feed-rate of alcohol solution of raw material and a fermentation volume, respectively.

$$R = F \cdot As - V \cdot dA/dt \qquad (1)$$

The value of $dA/dt$ in equation (1) can be expressed typically by equation (2) which is shown below. It seems that an alcohol consumption rate in a short time interval after the point of alcohol measurement can be proceeded with the value of R mentioned above. $A_o$ and $A_{-1}$ respectively designate alcohol concentration in a fermenting broth at the present measurement point and at the previous alcohol measurement. T is a time interval.

$$dA/dt = (A_0 - A_{-1})/T \qquad (2)$$

By instituting $Vo \cdot (Ac - Ao)/\alpha$ as a correction coefficient for getting alcohol concentration in a fermenting broth near a desirable alcohol concentration Ac, a feed-rate of alcohol solution of raw material in a short time interval from the present alcohol measurement to the next alcohol measurement may be calculated by equation (3).

$$Fo = \frac{F_{-1} \cdot As - Vo(Ao - A_{-1})/T + Vo(Ac - Ao)/\alpha}{As} \qquad (3)$$

Herein, Fo and F−1 respectively designate a feed-rate calculated at the point of alcohol measurement, and a feed-rate from the previous measurement point to the present measurement point. Vo is a fermentation volume at the present measurement.

On the basis of an alcohol measurement carried out for a short time interval as mentioned above, the alcohol concentration in a fermenting broth can be controlled accurately as described in the following Example 1 by calculating and controlling a coming new feed-rate of alcohol solution of raw material using equation (3) a point of alcohol measurement.

If the interval for alcohol measurement becomes longer, it becomes impossible to predict accurately the rate of alcohol comsumption, and therefore, the accuracy of control decreases. Thus, from 15 minutes to two hours is desirable as the interval for alcohol measurement. From 15 minutes to one hour is more desirable in order to increase the accuracy. Constant $\alpha$ as the correction coefficient should preferably be a value of from one to eight times the interval for alcohol measurement.

With respect to fermentation volume Vo in equation (3), appropriate apparatus for measurement of fermentation volume may be used for the direct measurement. In the case of continuous fermentation wherein the fermentation volume is not changed, the value of the fermentation volume may be initialized at the starting point. On the other hand, in the case of semicontinuous fermentation wherein the fermentation volume is variable, it is possible to calculate the fermentation volume by integral addition of the fed volume to the initial fermentation volume.

For the production of vinegar having high acetic acid concentration or enhancing the fermentation efficiency, it is necessary to change the alcohol concentration in the fermenting broth corresponding to the change of acetic acid concentration through the period of acetic acid fermentation. Hereinafter, the method of feeding alcohol solution as raw material in the case of semi-continuous batch fermentation is described.

Generally, one percent of acetic acid (weight-/volume) can be formed from one (volume/volume) of alcohol with no change of conversion efficiency from alcohol to acetic acid in acetic acid fermentation. Thus, if alcohol and acetic acid concentration are A and B, respectively, the sum of A and B means the maximum acetic acid concentration when all alcohol was converted into acetic acid. Hereafter this sum value is referred to as the total concentration C. For instance, in the case of the control of feed rate with the target point so that alcohol and total concentrations are controlled to be Aa and Ca respectively, when acetic acid concentration reaches up to Ba in semi-continuous batch fermentation, if alcohol, acetic acid and total concentrations are Ao, Bo and Co respectively, at a certain point in time, the volume (Qa) of alcohol solution necessary for reaching up to the acetic acid concentration Ba from this point is expressed by equation (4). Herein Cs designates the total concentration of alcoholic raw material.

$$Qa = Vo(Ca - Co)/(Cs - Ca) \qquad (4)$$

The time La by reaching up to acetic acid concentration Ba is calculated using equation $La = (Ba - Bo)/$ (Bo−B−1)/T) if fermentation proceeds in the current increasing rate of acetic acid concentration as similar to the calculation of alcohol consumption rate mentioned above. Herein, B−1 and T are the acetic acid concentration in the fermenting broth at the previous measurement, and the time interval for measurement, respectively. Thus, the necessary volume of alcoholic raw material must be fed within the period La. The feed rate Fo of alcoholic raw material is calculated using equation (5).

$$Fo = Qa/La \quad (5)$$

The acetic acid concentration in the fermenting broth at the point of measurement can be measured by taking out a sample automatically and by analysis using automatic titration equipment. On the other hand, it may be calculated using equation (6). Herein, $V-1$, $C-1$, $F-1$, $T$, $Cs$ and $Ao$ are the fermentation volume at the previous measurement, total concentration at the previous measurement, fed volume of alcoholic raw material at the previous measurement, the time interval for measurement, total concentration of alcoholic raw material and alcohol concentration at the present measurement, respectively.

$$Bo = \frac{V_{-1} \cdot C_{-1} + F_{-1} \cdot T \cdot Cs}{V_{-1} + F_{-1} \cdot T} - Ao \quad (6)$$

This means that the acetic acid concentration at the subsequent alcohol measurement may be calculated rapidly by means of a computer by measuring only the alcohol concentration if the fermentation volume and acetic acid concentration is once measured at a certain point in time during fermentation. In the particular case wherein high accuracy is desirable, acetic acid concentration may be corrected by a direct measurement at an appropriate time interval, for instance 24 to 48 hours according to necessity.

As mentioned above, it becomes possible to accurately control the alcohol concentration as described in the following experiment 2 by renewing repeatedly the target point when the acetic acid concentration reaches up near the target point Ba on the basis of calculation of the feed rate of alcoholic raw material using the increasing rate of acetic acid concentration and acetic acid concentration by measuring alcohol concentration automatically once every 15 minutes to two hours, more desirably 15 minutes to one hour.

According to this invention, not only automatic control of feed rate and alcohol concentration, but also control of aeration and agitation based on calculations of alcohol consumption rate and the increasing rate of acetic acid concentration can be performed.

Apparatus according to the present invention is described hereinbelow. Any type of apparatus capable of automatically performing a sampling operation responsive to a signal from a control computer and transferring the result into the computer can be used. Examples of such apparatus for carrying out automatic alcohol analysis are (1) gas chromatograph, (2) apparatus measuring alcohol permeated through gas permeable tubing (U.S. application Ser. No. 669,761, filed Nov 8, 1984, U.S. Pat. No. 4,656,140 corresponding to Japanese patent application No. 58-216218), (3) apparatus converting into concentration in a fermenting broth by monitoring exhaust gas from a fermentation tank with a mass spectrometer, etc. However, in the case of using a gas chromatograph, a problem often occurs because large parts of the apparatus for automatic sampling are constituted by mechanical parts and rapid deterioration thereof occurs due to the introduction samples and due to the microorganisms, saccharides in the fermenting broth. Thus, the necessity of maintenance is quite frequent in a system using a large number of mechanical parts. In addition, the number of samples capable of being measured within a specified time interval is low because of a long retention time of acetic acid contained in the fermenting broth. This means that the interval between measurements must be increased. However, long time intervals interfere with control of fermentation in the case of controlling multiple fermentation tanks. On the other hand, apparatus using gas permeable tubing described in said U.S. application Ser. No. 669,761, filed Nov. 8, 1984, U.S. Pat. No. 4,656,140 (corresponding to Japanese patent application No. 58-216218) has two advantages, such as rapid response time and easy maintenance. For example, maintenance is required only about once every 6 months or one year because of no mechanical parts in the sampling system and slow deterioration of the sensor and column since only the gas component is introduced into the column, even though the column is used for absorption of acetic acid.

Apparatus using a mass spectrometer has also the same two advantages as apparatus using gas permeable tubing because of no mechanical parts in the sampling system and direct introduction of sample exhaust gas from a fermentation tank with no special columns for separation and absorption of acetic acid. However, it has a disadvantage that temperature correction is necessary for conversion of alcohol concentration in the vapor into that in the fermenting broth, and it is expensive.

Since this invention deals with a fermentation process performing continuously for more than several months with 24 hours performance, easy maintenance and rapid response for increasing the accuracy of fermentation control are required for the apparatus for automatic alcohol measurement.

For the above reasons, the apparatus described in U.S. Ser. No. 669,761, U.S. Pat. No. 4,656,140, using gas permeable tubing or apparatus using a mass spectrometer is more desirable as apparatus for automatic alcohol measurement in performance of this invention. Especially, the apparatus using gas permeable tubing is preferable because said apparatus is not so expensive. Any type of apparatus functioning to control the feed rate under the direction of a control computer may be used as apparatus for the feeding of alcoholic raw material. For example, a variable pump able to vary the feed rate by means of a remote controller or an automatic valve able to adjust the degree of open and close thereof by flow meter mounted in the system equipped with the automatic valve can be used. With these devices, the alcoholic raw material is fed to the system naturally from a tank mounted at a higher place so that the alcoholic raw material flows under the influence of gravity. A computer for control functions performs not only the calculations necessary for the performance of this invention, but also has general control over (1) apparatus for automatic alcohol measurement, (2) feed of alcoholic raw material, and further, if necessary, (3) automatic titration apparatus, (4) integral flow meter, (5) temperature controller and (6) apparatus for charge and discharge. Furthermore, the computer requires the function to be able to communicate input and output signals between peripheral equipment. For example, a programmable controller (computer) can be used as the apparatus having the functions mentioned above.

Referring to FIG. 1, the present invention is described in more detail. As shown in FIG. 1, six fermentation tanks 1 are provided, each having a respective solenoid valve 2 coupled thereto. A solenoid 2 for a respective fermentation tank 1 in which the alcohol concentration must be measured first is selected from the six solenoids 2 for selection of sampling through sampling line 5. A sample of the fermenting broth from the selected tank 1 is then introduced into apparatus for automatic alcohol measurement 3 by sampling pump 6. Measurement apparatus 3 then measures the alcohol concentration of the sample. The result of the measurement is transferred to the control computer 24 over electrical line 30. According to necessity, outputs of measurement from flow meter 8, integral flow meter of alcoholic raw material 14 and automatic titration apparatus 4 for measurement of acetic acid concentration are also transferred to the control computer 24. Then, the feed rate is calculated by internal programmed calculation in the computer 24 using those measured data and set values which were input in advance, and appropriate signals for adjustment of the feed rate of alcoholic raw material are output to remote controlled pump 15 used as an apparatus for feeding alcoholic raw material.

In the case of semi-continuous batch fermentation, a signal for operation is output from computer 24 to apparatus for discharge such as a solenoid for discharge 13 and pump for discharge 12 when the concentration of acetic acid and alcohol match with the set values for discharge. Subsequently, a signal for operation is output to apparatus for charge such as solenoid 18 for charge and a pump for charge 17. Particularly, in the case of the production of vinegar having high acetic acid concentration by lowering the fermentation temperature with an increase of acetic acid concentration, for example the method described in Japanese patent application Kokai Koho No. 56-55193, the system able to input a desirable set temperature into temperature controller 25 from control computer 24 can be added according to necessity. As shown in FIG. 1, also provided are a sampling pump 7 for measurement of acetic acid concentration, an agitator 9, an air pipe 10, and a solenoid 11 for cooling. Further provided are a solenoid 16 for feeding of alcoholic raw material and a pipe line 19 for feeding alocholic raw material, respectively, to the tank 1. Also provided are a pipe line 20 for charge, a pipe line 21 for discharge, a solenoid 22 for discharge, a pipe line 23 for discharge, an exhaust pipe 26, a thermometer 27 and a cooling pipe 28. The same apparatus as shown in the left side of FIG. 1, associated with the enlarged tank 1 shown in detail, is also provided individually for the other fermenting tanks 1, so that they can all be individually and independently controlled.

EXAMPLE 1

Continuous acetic acid fermentation controlling alcohol concentration in a fermenting broth are performed according to this invention using three aeration-agitation fermentation tanks. In this embodiment, apparatus described in said U.S. Ser. No. 669,761, using gas permeable tubing as apparatus for alcohol measurement, was used and samples were taken out from, in turn, three different fermentation tanks 1. Remote controlled pumps able to vary the feed rate of the alcoholic raw material were installed on each fermentation tank as an apparatus for feeding alcoholic raw material and a programmable controller (computer) 24 (hereinafter called PC) was used as the control computer. Prior to the start of fermentation, a calibration curve obtained using a standard alcohol solution with known concentration was memorized in the PC 24. In addition, 2.0 hr. 18 kl. 0.5%, 6.5%, 0.5 hr and −0.2%/hr were memorized in PC 24 as each value of $\alpha$, fermentation volume, desired alcohol concentration in the fermentating broth, alcohol concentration of the alcoholic raw material, interval for measurement and initial value of $(A_o - A - 1)/T$ in equation (3), respectively.

Seed culture, alcoholic raw material and fermenting broth (total volume 18 kl) were charged into each fermentation tank 1, and the temperature of the fermenting broth was kept to be 30° C. Fermentation was performed under the condition of agitation (by agitator 9) and aeration (by pipe 10). When the start of fermentation was confirmed by the increase of the acetic acid concentration in the fermenting broth of the first fermentation tank from 4% to 5.9%, the control of the feed rate of alcoholic raw material was started. Fermenting broth was first taken out from the first fermentation tank using pump 6 and introduced into automatic alcohol analyzer 3. The result of measurement by automatic alcohol analyzer 3 was further input into an A/D converter (the A/D converter is required when the output of analyzer 3 is analog rather than digital) of PC 24 and the alcohol concentration was determined to be 0.603% according to the calibration curve. The feed rate was calculated subsequently on the basis of equation (3) using the alcohol concentration measured above.

$$(0 \times 6.5 - 18000 \times (-0.2) + 18000 \times (0.5 - 0.603)/2)/6.5 = 411$$

This calculated data was then transferred to apparatus 15 for feeding alcoholic raw material through a D/A converter (if an analog drive signal is required) of the PC 24, so as to control the feed rate to be 411 liters per hour. Subsequently, the alcohol concentrations in the second and third fermentation tanks were measured and each feed rate was calculated similarly. The alcohol concentration in the first fermentation tank was measured to be 0.508% at 30 minutes after the start of fermentation control and the alcoholic raw material feed rate was determined to be 926 liters per hour on the basis of equation (3).

$$(411 \times 6.5 - 18000 \times (0.508 - 0.603)/0.5 + 18000 \times (0.5 - 0.508)/2)/6.5 = 926$$

Figure 3:
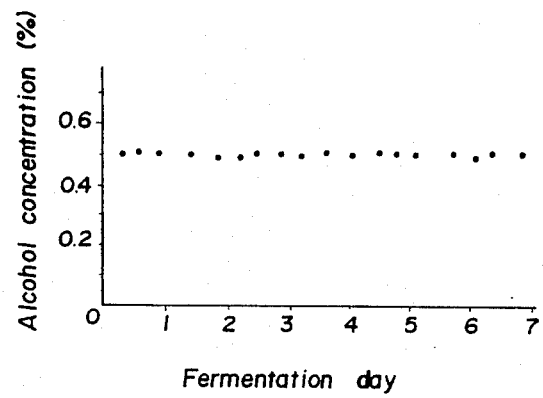
FIG. 3 is a graph showing the relation between fermentation days and alcohol concentration.

In such a way, the alcohol concentration in each fermentation tank was measured every 30 minutes and the alcoholic raw material feed rate was controlled. As the result, the alcohol concentration in the fermenting broth in the first fermentation tank was controlled accurately within the range of 0.490 to 0.505% during seven days of fermentation, except for the period immediately after the start of fermentation, as shown in FIG. 3. Similar accurate control of the other two fermentation tanks was also accomplished.

Figure 2:
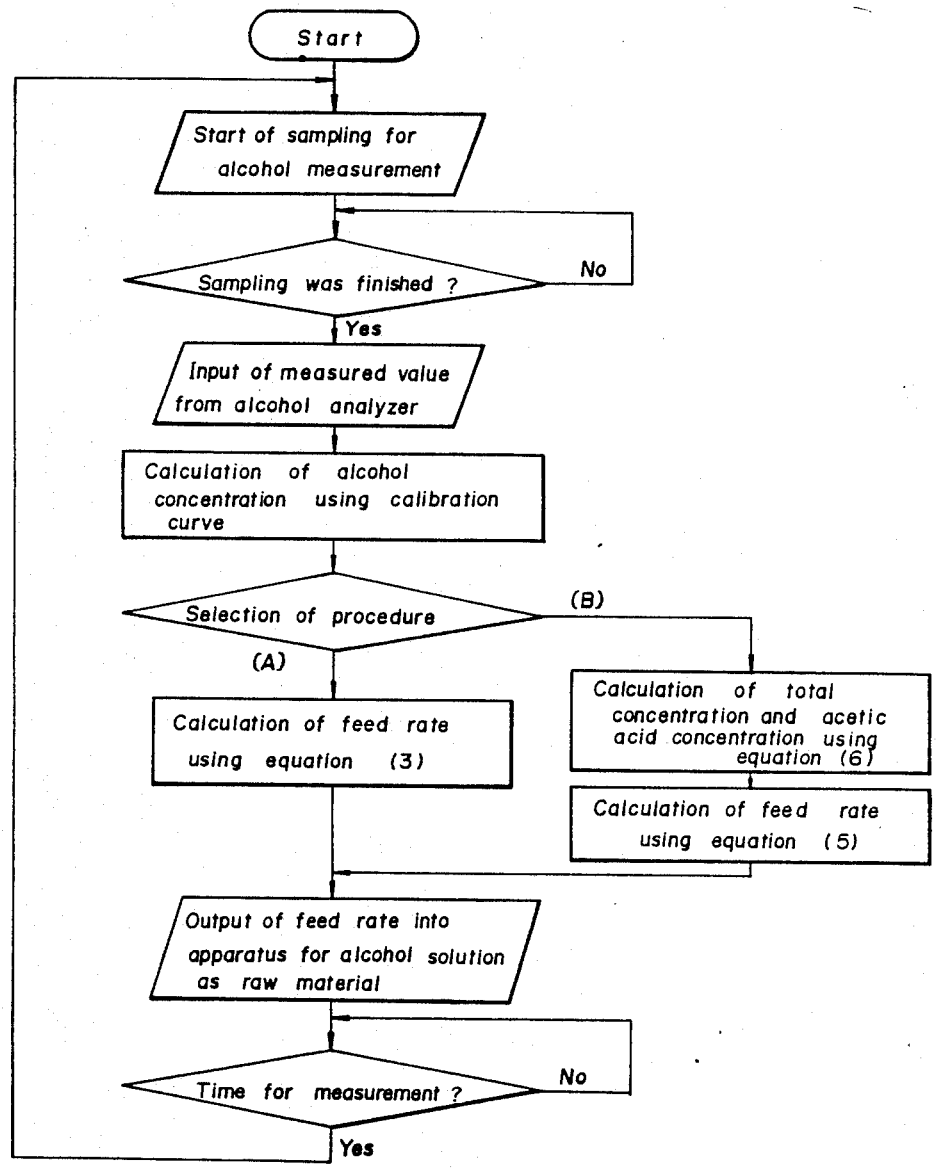
FIG. 2 is a schematic flow chart of the control method for controlling the feed rate of alcohol solution as raw material (hereinafter referred to as (alcoholic raw material).

FIG. 2 shows a flow chart of the operation of the system which should now be apparent from the foregoing discussion of the apparatus and of Example 1. The flow chart of FIG. 2 will become even more clear from the following.

EXAMPLE 2

The vinegar production process may be semi-continuous fermentation described in Japanese patent application Kokai Koho No. 56-55193. Japanese No. 56-55193 shows a production method for vinegar having a high acetic acid concentration in which the temperature of the fermenting broth is lowered, in turn, as the acetic acid concentration in the fermenting broth increases. The automatic control of feed rate of alcoholic raw material and the change of fermentation temperature in the present invention is carried out in this Example 2 under the condition that the alcohol concentration in the fermenting broth is kept to be 2% until the acetic acid concentration reaches up to 15% and the alcohol concentration was lowered, in turn, as the acetic acid concentration increases after that.

A fermentation tank of 20 kl of working volume has a mass spectrometer mounted thereto as apparatus for automatic alcohol measurement. A remote controlled pump is provided as apparatus for automatic alcohol measurement. A remote controlled pump is provided for feeding alcoholic raw material to the fermentation tank, an integral mass flow meter is provided for measurement of fed volume of alcoholic raw material, a thermometer is provided for temperature control, an automatic titration apparatus is provided for measurement of acetic acid concentration, and pumps for discharge and charge were used, as shown in FIG. 1. These apparatuses mentioned above were connected electrically with PC (computer 24 in FIG. 1).

The values of time interval for alcohol measurement, alcohol and total concentrations of alcoholic raw material, initial volume of fermentation, initial increasing of acetic acid concentration were set 30 minutes, 50%, 58%, 15 kl, and 0.2%/hr., respectively. With respect to the relation between acetic acid and total concentrations at the target points in fermentation, 15% and 17% at the first point, 17% and 18.5% at the second point, 19% and 20% at the third point and 21% and 21.5% at the fourth point were set, respectively. As to the change of temperature, 30° C. by the first point, 28° C. by the second point, 26° C. by the third point and 25° C. by the fourth point were set, respectively, 0.3% and 20.8% were set as alcohol concentration and total concentration at the point of discharge, respectively. Calibration curves at various temperatures were measured by means of introducing exhaust gas to the alcohol analyzer 3 from 2 liters mini-farfermentor containing standard alcohol solution with known concentration. All the values mentioned above were memorized in PC 24.

The fermentation volume was calculated by the programmed calculation in PC 24 by means of integral addition of the fed volume to the initial fermentation volume which was input initially into PC 24. The acetic acid concentration was measured automatically by means of the automatic titration apparatus every 24 hours. Within this time interval, the acetic acid concentration was calculated by calculation with PC 24 based on equation (6).

Fifteen kiloliters of fermentation mash consisting of seed culture and alcoholic raw material containing fermentation nutrient was charged into fermentation tank 1 and the aeration-agitation and the fermentation control were started simultaneously (by PC 24) under the condition that temperature was controlled to be 30° C. The alcohol concentration in the fermenting broth was determined to be 2.50% on the basis of measurement of the alcohol concentration in the exhaust gas by introducing it into automatic alcohol analyzer 3 and inputting the result with a temperature of the fermenting broth into PC 24. Further, the concentration of acetic acid was determined to be 6.50% by means of the automatic titration apparatus. On the basis of this result, the feed rate of the alcoholic raw material was calculated by equation (5).

$$(15000 \times (17.0 - 9.0)/(58.0 - 17.0))/(15.0 - 6.5)/0.2) = 68.9$$

Then, the feed rate of the alcoholic raw material was controlled to be 68.9 l/hr. At 30 minutes after the previous measurement, the alcohol concentration was once again measured, and the alcohol concentration was determined to be 2.49%. The acetic acid concentration was determined to be 6.62% using equation (6).

$$(15000 \times 9.0 + 34.5 \times 58.0)/(15000 + 34.5) - 2.49 = 6.62$$

The feed rate of alcoholic raw material was calculated by using equation (5) and controlled to be 82.9 l/hr.

$$\text{Feed rate} = (15034.5 \times (17.0 - 9.11)/(58.0 - 17.0))/((15.0 - 6.62)/(6.62 - 6.5)/0.50)) = 82.9$$

In such a way, the alcohol concentration was measured and the feed rate of alcoholic raw material was controlled every 30 minutes.

Although alcohol, acetic acid and total concentration were calculated to be 2.18%, 12.38% and 14.56%, respectively, at 24 hours after the start of control, acetic acid and total concentration were corrected to be 12.40% and 14.58%, respectively, on the basis of direct measurement of acetic acid concentration by the automatic titration apparatus.

Figure 4:
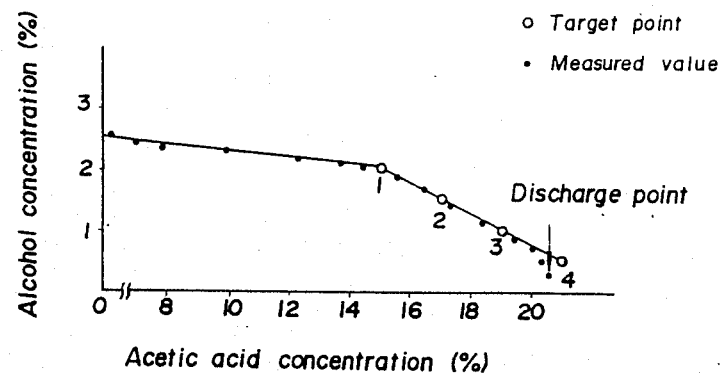
FIG. 4 is a graph showing analytical data of alcohol and acetic acid concentrations in time course.

The set point was moved from the first point to the second point when the acetic acid concentration reached up to 14.8% which is lower than the set value, 15% at the first point and direction was transferred to the temperature controller 25 from PC 24, so that there was a change of temperature of the fermenting broth from 30° C. to 28° C. when the acetic acid concentration reached up to 15%. In such a way, the set point was successively changed to the next point and simultaneously the feed rate of alcoholic raw material and temperature were controlled. Finally, the total concentration was matched with that of the discharge on the way to the fourth point, and the feeding of alcoholic raw material was stopped by direction from PC 24. Subsequently, fermentation was continued and discharge was performed by direction from PC 24 when the alcohol concentration became 0.3% which is equal to the condition of the discharge. After the finish of discharge, the mash for the next fermentation was subsequently charged. The time course of analytical data of alcohol and acetic acid concentrations during fermentation is shown in FIG. 4, which indicates that the alcohol concentration in the fermenting broth was controlled accurately around the pre-set value.

The contents of all of the publications referred to herein are incorporated herein by reference.

While the invention has been described with respect to specific apparatus and specific method steps, various modifications and alterations can be made within the scope of the appended claims.

We claim:

1. In apparatus for automatically controlling the feed rate of an alcohol solution as raw material in a process for producing vinegar from a fermenting broth in a fermentation tank, the improvement comprising:

an automatic alcohol analyzer for measuring the alcohol concentration in said fermenting broth in said fermentation tank;

feeding means for feeding alcohol solution as raw material to said fermentation tank;

control computer means coupled to said analyzer and to said feeding means for energizing said alcohol analyzer to initiate an automatic alcohol concentration measurement and for receiving an output signal from said analyzer corresponding to the measured alcohol concentration, said control computer means including calculating means for calculating a feed rate of alcohol solution as raw material to said fermenting broth responsive to said output from said alcohol analyzer, and for generating an output signal responsive to said calculations to control operation of said feeding means to feed alcohol solution as raw material to said fermenting broth so as to control the alcohol concentration in said fermenting broth at a desirable concentration, said control computer means including means for periodically causing said analyzer to measure said alcohol concentration in said fermenting broth at given intervals over a plurality of cycles of measurement.

2. The apparatus of claim 1, wherein said control computer means includes means for calculating said feed rate and for controlling the alcohol concentration in said fermenting broth on the basis of a difference between a measured alcohol concentration in said fermenting broth and a desirable alcohol concentration and the alcohol consumption rate calculated during each of said cycles by said control computer means.

3. The apparatus of claim 1, wherein said control computer means includes means for calculating said feed rate of alcohol solution as raw material to said fermenting broth so as to control the alcohol concentration in said fermenting broth at a predetermined desirable concentration according to acetic acid concentration on the basis of increasing rate of acetic acid concentration, acetic acid concentration and total concentration in said fermenting broth which are calculated by said control computer means during each of said cycles.

4. The apparatus of claim 1, wherein said analyzer, feeding means and control computer means are electrically interconnected.

5. The apparatus of claim 1, wherein said control computer means includes means for causing said analyzer to measure said alcohol concentration at an interval of two hours or less.

6. The apparatus of claim 5, wherein said interval is between fifteen minutes and one hour.

7. The apparatus of claim 1, wherein said apparatus comprises a plurality of fermentation tanks, each containing a fermenting broth, and wherein said analyzer is coupled to each of said tanks for selectively measuring the alcohol concentration in respective tanks responsive to signals from said control computer means, and said feeding means is selectively coupled to each of said tanks to feed said alcohol solution as raw material to said respective tanks responsive to control signals from said control computer means.

8. The apparatus of claim 7, wherein said control computer means causes said analyzer and feeding apparatus to be associated with each of said plurality of tanks on a cyclical basis at different respective times.

9. The apparatus of claim 1, further comprising a titration apparatus for measuring the acetic acid concentration in said fermenting broth.

* * * * *